(12) United States Patent
Magneson et al.

(10) Patent No.: US 8,545,808 B2
(45) Date of Patent: Oct. 1, 2013

(54) COMPOSITIONS FOR RADIOLABELING DIETHYLENETRIAMINEPENTAACETIC ACID (DTPA)-DEXTRAN

(75) Inventors: Gerald Ross Magneson, Needham, MA (US); Richard Cushman Orahood, Delaware, OH (US)

(73) Assignee: Navidea Biopharmaceuticals, Inc., Dublin, OH (US)

( * ) Notice: Subject to any disclaimer, the term of this patent is extended or adjusted under 35 U.S.C. 154(b) by 0 days.

(21) Appl. No.: 13/461,306

(22) Filed: May 1, 2012

(65) Prior Publication Data

US 2012/0213700 A1 Aug. 23, 2012

Related U.S. Application Data

(62) Division of application No. 12/362,778, filed on Jan. 30, 2009, now abandoned.

(51) Int. Cl.
*A61K 51/00* (2006.01)
*A01N 59/16* (2006.01)

(52) U.S. Cl.
USPC .......................... 424/1.61; 424/650

(58) Field of Classification Search
None
See application file for complete search history.

(56) References Cited

U.S. PATENT DOCUMENTS 4,364,920 A * 12/1982 Winchell ............... 424/1.53
6,409,990 B1 * 6/2002 Vera ..................... 424/9.35

FOREIGN PATENT DOCUMENTS

EP 0516873 * 6/1991

OTHER PUBLICATIONS

Verbeke et al. "Development and evaluation of a kit formulation for the preparation of 99mTc-DMP-HSA, a new tracer agent for radionulide ventriculography", Nuclear Medicine & Biology, 24, 1997, pp. 571-578.*

* cited by examiner

*Primary Examiner* — Daniel Sullivan
*Assistant Examiner* — Melissa Javier
(74) *Attorney, Agent, or Firm* — Roger A. Gilcrest (57) ABSTRACT

The subject invention relates to the compositions for radiolabeling Diethylenetriaminepentaacetic Acid (DTPA)-dextran with Technetium-99m and for stabilizing the DTPA-dextran Cold Kit. The composition contains Stannous Chloride ions to reduce $^{99m}$Tc-pertechnetate, Ascorbic Acid to reduce stannic ions to stannous ions to maintain a reducing environment, α,α-Trehalose to add bulk and to stabilize the lyophilized composition without interfering with the radiochemical yield, and Glycine to transchelate Technetium-99m under highly acidic conditions to facilitate radiolabeling DTPA-dextran with high radiochemical purity. In addition, the invention pertains to methods for making and using the compositions. The reconstitution of the lyophilized composition by $^{99m}$Tc-pertechnetate, resulting in radiolabeled $^{99m}$Tc-DTPA-dextran in a composition between pH 3 to 4. This invention contains a Diluent vial, which when used will shift the pH to a moderately acidic pH, which would provide less pain on injection and ease-of-use to clinical practitioners for adjusting its potency.

8 Claims, 12 Drawing Sheets

COMPOSITIONS FOR RADIOLABELING DIETHYLENETRIAMINEPENTAACETIC ACID (DTPA)-DEXTRAN

CROSS-REFERENCE TO RELATED APPLICATIONS

This application is a divisional of U.S. application Ser. No. 12/362,778, filed Jan. 30, 2009, which is hereby incorporated in its entirety herein by reference.

STATEMENT REGARDING FEDERALLY SPONSORED RESEARCH

Not applicable.

BACKGROUND

The present disclosure relates to the field of oncology and more particularly to the radiolabeling of a cancer detection agent.

Sentinel node biopsy is rapidly gaining acceptance as a common practice for melanoma and breast cancer diagnosis (Vera, D. R. et al. (2001) *J. Nucl. Med.* 42, 951-959). This technique has not been standardized; it typically involves the use of a $^{99m}$Tc-colloid and a blue dye. The radioisotope, $^{99m}$Technetium, that is used in the colloid imaging agent and in the current invention, has several desirable properties: its ready availability, relatively low cost, excellent imaging quality, and its short half-life of 6 hours. This radiotracer is employed preoperatively to ascertain the location of the sentinel node and, then, it is used intraoperatively to pinpoint the dissection of the sentinel node(s). The blue dye, which is cleared rapidly through the lymph channels and nodes, is used to visually confirm the selection of the radioactive node as the sentinel node. Because this biopsy procedure varies with individual practitioners, it is difficult to train practitioners with a consistent skill set and consequently, these biopsies result in a wide range of reported false-negative rates (i.e., 0 to 12%—see Vera, D. R. ibid.).

There is another hurdle to standardization of this sentinel node biopsy technique. There is no blue dye or $^{99m}$Tc-labeled agents specifically designed for sentinel node detection or extraction. Currently, the FDA (U.S. Food and Drug Administration) has not approved any dye, or $^{99m}$Tc-labeled agent for sentinel node diagnosis. Thus, the following radiopharmaceutical agents are used off-label: $^{99m}$Tc-sulfur colloid, filtered $^{99m}$Tc-sulfur colloid, $^{99m}$Tc-antimony trisulfide, and several preparations of $^{99m}$Tc-labeled albumin microcolloids. (Note: Colloids are non-targeted particles that are sticky.) None of these agents display ideal properties of rapid injection site clearance or high sentinel node extraction (Hoh, C. K., et al. (2003). *Nucl. Med. Biol.* 30, 457-464).

Hence, the development of a nuclear imaging diagnostic kit that is designed to meet the goals of optimal sentinel node detection (i.e., rapid injection site clearance and low distal lymph node accumulation) is an unmet medical need in breast and melanoma cancer treatment.

BRIEF SUMMARY

The present disclosure provides a composition containing a dextran conjugated with a bifunctional chelating agent, such as, DTPA, with ease of use as an "instant" kit involving a single lyophilized vial and a liquid diluent vial, having high radiochemical purity upon radiolabeling. The present disclosure also provides long-term storage stability, as well as sufficient reconstituted stability to facilitate its pharmaceutical or clinical use for ease of manipulation and administration as a diagnostic imaging agent.

Upon addition of Sodium $^{99m}$Tc-pertechnetate, the present disclosure displays high radiochemical purity (i.e., >90% $^{99m}$Tc-DTPA-dextran purity) for the bifunctional ligand, DTPA, which are conjugated to a number of amino-terminated leashes on to a dextran molecule via an amide bond with one of its five carboxylic arms. While free DTPA undoubtedly coordinates all five of its deprotonated carboxylic groups to bind to heavy metal ions, such as, for example, $^{111}$Indium, as a potential octadentate ligand (also contains three nitrogen atoms—see H. R. Maecke, et al. (1989) *J. Nucl. Med.* 30, 1235-1239), the heptadentate DTPA binds with decreased thermodynamic stability, which makes it more susceptible to competition for binding $^{99m}$Tc ions, possibly resulting in decreased radiochemical purity.

The high radiochemical purity of $^{99m}$Tc-DTPA-dextran was achieved by decreasing the pH to between about 2 and 4, screening for non-competing constituents and identifying the ideal transchelator, Glycine (which also serves as a pH buffer), and utilizing the following facts: (1) the distribution of competing ligands for $^{99m}$Tc is determined by association rate constants, and (2) the dissociation rate constants for $^{99m}$Tc from its DTPA-dextran complex is very slow and pH-dependent. Hence, the high efficiency of radiolabeling DTPA-dextran is enhanced by the transient binding to Glycine under highly acidic conditions, Glycine transferring the radioisotope to DTPA-dextran that more avidly binds it and the retention of the Technetium-99m (due to its slow dissociation rate constant) after the pH of this "instant" kit is shifted to mildly acidic conditions by its diluent.

The present disclosure further provides a phosphate buffered saline diluent, enabling patient comfort by shifting pH from harsh acidic conditions (i.e., pH between about 3 and 4), which would cause pain on injection, to moderately acidic conditions (i.e., pH>~5), which would be well tolerated (M. Stranz and E. S. Kastango (2002) *Int. J. Pharm. Compound.* 6(3), 216-220).

The present disclosure further provides a reducing agent, such as, for example, L-ascorbic acid, which further stabilizes a radiolabeled DTPA-dextran preparation containing excess stannous or stannic ions, preventing the formation of Sn-colloids or other radiochemical impurities, such as, $Sn^{4+}$. The present disclosure yet prevents the oxidative degradation of the drug substance and its constituents and the autoradiolysis of the radiolabeled drug product by containing L-ascorbic acid in the formulation.

Furthermore, the present disclosure further provides a stable and esthetically pleasing environment for the DTPA-dextran in an amorphous disaccharide lyophilization cake, allowing for quick reconstitution with Sodium $^{99m}$Tc-pertechnetate and addition with a buffered saline diluent to produce a clear, non-particulate liquid for ease of use. The present disclosure also provides an inert gaseous headspace by backfilling the lyophilized vials with pharmaceutical-grade nitrogen gas, further stabilizing the stannous ions to provide an excess capacity over the storage lifetime of this invention for reducing Sodium $^{99m}$Tc-pertechnetate (or, $^{99m}$TcO$_4^-$).

The present method, then, is an improved method for generating high radiochemical purity $^{99m}$Tc(III) (and possibly, $^{99m}$Tc(IV)) complexes of DTPA-dextran with a single, lyophilized vial that is further reconstituted with pH-buffered Diluent to shift final solution pH, resulting in a solution that is stable for at least 6 hours and that facilitates patient comfort (Russell, C. D. (1980) *J. Nucl. Med.* 21, 354-360; Russell, C.

D. and Speiser, A. G. (1982) *Int. J. Appl. Radiat. Isot.* 33, 903-906). The formulation of the lyophilized cold kit for DTPA-dextran is an "instant" kit, stabilizing the stannous chloride necessary to reduce Sodium $^{99m}$Tc-pertechnetate in a solid white lyophilized cake under a nitrogen environment, which has long-term storage stability. This kit generates high radiochemical purity by the $Sn^{2+}$ reduction of $^{99m}$Tc-pertechnetate under highly acidic conditions, while maintaining the $^{99m}$Technetium-DTPA-dextran complex in greater than 90% radiochemical yield following dilution with a phosphate-buffered saline solution to shift the reconstituted solution pH toward neutrality.

BRIEF DESCRIPTION OF THE DRAWINGS

For a fuller understanding of the nature and advantages of the present process, composition, and kit, reference should be had to the following detailed description taken in connection with the accompanying drawings, in which.

The drawings will be described in greater detail in the examples below.

DETAILED DESCRIPTION

The key to development of a commercial "instant" kit for sentinel node diagnosis is the rational design of an imaging agent that will possess the properties required for optimal sentinel node detection. These properties are a small molecular diameter and high receptor affinity, yielding a radiopharmaceutical agent with a rapid injection site clearance rate and low distal lymph node accumulation (Vera, D. R. ibid.). In the present invention, the drug substance that is employed uses a dextran platform to deliver the radiolabel. The dextran backbone is a pharmaceutical-grade, average molecular-weight polymer of about 9,500 that is very hydrophilic, lacking in charge, and flexible. All these physical properties reduce migration across membrane walls, which facilitate rapid injection site clearance. The dextran polymer is conjugated to amine-terminated tethers that are coupled to DTPA groups, giving the molecule high receptor affinity to complex $^{99m}$Technetium. The high signal density of $^{99m}$Tc-DTPA-mannosyl-dextran enables better detection of the sentinel node(s) due to a higher signal-to-background ratio.

The addition of mannosyl groups, which are conjugated to other amine-terminated tethers, gives the binding specificity to DTPA-mannosyl-dextran to differentiate it from its alternative, non-targeted imaging agents. DTPA-mannosyl-dextran binds avidly to mannose-terminated glycoprotein receptors in vitro (Vera, D. R. ibid.). In rabbit biodistribution studies, it was shown that $^{99m}$Tc-DTPA-mannosyl-dextran diffuses into lymph channels, flows to the sentinel node, and binds to mannose-binding glycoprotein receptors in macrophages and dendritic cells present in the sentinel node (Hoh, C. K. ibid.; Fiete, D. and Baenziger, J. U. (1997) *J. Biol. Chem.* 272(23), 14629-14637; Ramakrishna, V. et al. (2004) *J. Immunol.* 172, 2845-2852). Thus, $^{99m}$Tc-DPTA-mannosyl-dextran is a superior targeted $^{99m}$Tc-labeled diagnostic agent for sentinel node detection (Hoh, C. K., ibid.). While the pre-clinical and Physician Phase I trials of $^{99m}$Tc-DTPA-mannosyl-dextran successfully employed a radiolabeling procedure that used multiple fluid transfers and multiple vials, this dosing format would have been undesirable for commercial usage.

In order to commercialize this important nuclear imaging agent, the composition (formulation) and methods for making this composition of Lymphoseek® ligand drug product have been developed, which is the subject of the present disclosure. The development of a $^{99m}$Technetium-labeled nuclear imaging "instant" kit is a delicate counterbalance between high radiochemical efficiency and the formation of non-specific $^{99m}$Tc-labeled materials (i.e., $^{99m}$Tc-colloid, or $^{99m}$Tc-labeled formulation excipients). Also, reduced $^{99m}$Technetium needs to be prevented from reoxidating to $^{99m}$TcO$_4^-$. Hence, a lyophilized formulation was developed to stabilize stannous ions under an inert nitrogen environment.

In this disclosure, the composition accomplishes this delicate balancing act by utilizing a newly identified transchelator, Glycine, under highly acidic conditions. A transchelator is a weak chelator that transiently binds reduced $^{99m}$Technetium, facilitating the transfer of this radioisotope to a stronger chelator, or ligand. The ligand for reduced $^{99m}$Technetium is derivatized diethylenetriaminepentaacetic Acid (DTPA), a heptadentate bifunctional ligand that coupled to the dextran amine-terminated tether by one of its five carboxylic groups. This ligand is well known to the practitioners of the art. It has been incorporated into "instant" kits for radiolabeling peptides and proteins (Hansen et al., U.S. Pat. No. 5,328,679; Zamora and Marek, U.S. Pat. No. 6,685,912 B2; and Winchell, U.S. Pat. No. 4,364,920) In these US patents, DTPA is a bifunctional chelator conjugated to peptides and proteins, usually as an anhydride form covalently attached through its carbon backbone.

These patents describe a spectrum of transchelators known to the art, such as, for example, Citrate, Tartrate, Phosphate, Phosphonate, Glucoheptonate and even, Ascorbic Acid. But, these transchelators are largely employed in mildly acidic to neutral pH formulations and can interfere with radiolabeling the active ingredient with high efficiency. The optimal pH for using Ascorbic Acid as a transchelator is from pH 4.5 to 6.2 (Liang et al. (1987) *Nucl. Med. Biol.* 14, 555-562). This stems from the pK$_a$ of its carboxylic group, pH 4.10 (*CRC: Handbook of Chemistry and Physics, 75$^{th}$ Edition*, David R. Lide, Ph.D. (CRC Press, London)). The pK$_a$ of the carboxylic group of Glycine is 2.34. Its carboxylic group remains functional under highly acidic conditions (e.g., partially deprotonated at pH 2 and is fully deprotonated at pH 4). At the preferred embodiment in this disclosure, Ascorbic Acid is fully protonated. Thus, the composition reduces the potential interference of ascorbic acid, utilizing the beneficial properties of this antioxidant, while employing Glycine as an optimal transchelator.

When the covalently coupled DTPA binds reduced $^{99m}$Technetium, the probable principal oxidation state is $^{99m}$Tc(III) under acidic conditions, which should result in stable complex with a zero net charge (Russell, C. D. (1980) *J. Nucl. Med.* 21, 354-360). The liquid composition at pH 2 radiolabels DTPA-dextran successfully, shifting to a higher pH on the addition of the diluent. But, at pH lower than, or equal to 2.7, the DTPA groups are fully protonated, possibly resulting in the total collapse of the lyophilized formulation at pH 2 (Hnatowich, D. J. et al. (1995) *J. Nucl. Med.* 36, 2306-2314). Hence, the preferred embodiment is to have the composition range from pH about 3 to about 4 to enable high radiochemical efficiency, while shifting pH to greater than about pH 5 on dilution of the reconstituted "instant" kit with phosphate-buffered saline Diluent, which would be well tolerated by patients. In this application, all ingredients are desired to be USP-grade (United States Pharmacopeia). Also, "q.s." has its standard pharmaceutical meaning of "as much as is sufficient".

EXAMPLES

Example 1

Elution Profiles of $^{99m}$Tc-Labeled DTPA-Mannosyl-Dextran and DTPA

Figure 1:
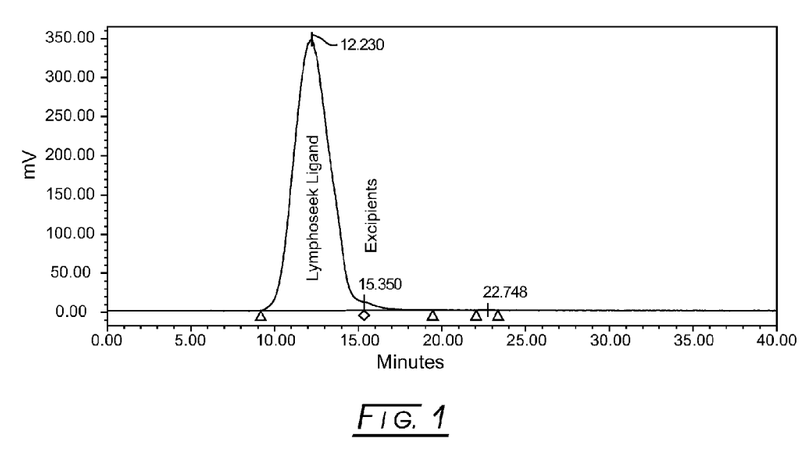
FIG. 1 shows a typical Size Exclusion Chromatography (SEC) elution profile for reconstituted $^{99m}$Technetium-labeled Lymphoseek® (registered trademark of Neoprobe Corporation, Dublin, Ohio U.S. Pat. No. 6,409,990) ligand drug product ($^{99m}$Tc-DTPA-mannosyl-dextran)

FIG. 1 shows a typical elution profile for reconstituted $^{99m}$Technetium-labeled Lymphoseek Ligand Drug Product ($^{99m}$Tc-DTPA-mannosyl-dextran), Lot NMK001, measured by a radioactivity (NaI, set at 1000 cps/Volt) detector using Size Exclusion Chromatography (SEC). The conditions for this SEC radiochemical purity method are as follows: a TSK-gel column, Tosoh Bioscience, G3000PW$_{XL}$ (7.8×30 cm, 6 μm, with a column temperature of 25±5° C.) is employed with an isocratic mobile phase of 50 mM phosphate buffer, pH 7.2, and 300 mM sodium chloride. The lyophilized vial is reconstituted with 0.8 cc of 10 milliCuries of $^{99m}$Tc-pertechnetate, mixed, and allowed to radiolabel for at least 10 minutes at ambient room temperature prior to partially neutralizing the sample in 0.2 cc Phosphate-buffered saline. A refrigerated drug product sample, 15 μL, is injected and run at 0.6 mL/minute for a run time of 40 minutes; the retention time of the $^{99m}$Tc-DTPA-mannosyl-dextran ($^{99m}$Tc-DMD) peak is about 12 to 12.5 minutes, stretching between 9 and 15 minutes with a tailing shoulder of $^{99m}$Tc-labeled excipients eluting at a radioactive peak of about 15 to 15.5 minutes.

The elution profile is very similar to that the potency method using the same column and mobile phase, employing a Refractive Index detector (due to the absence of a UV/VIS absorbance). The broad elution peak for $^{99m}$Tc-DTPA-mannosyl-dextran is a result of the heterogeneity of the dextran polymer, which is further acerbated by the heterogeneity of the coupling of mannosyl and DTPA groups to amino-terminated leases on dextran (Vera, D. R. et al. (2001) *J. Nucl. Med.* 42, 951-959). The goal of the DTPA-mannosyl-dextran formulation was to achieve greater than 95% radiochemical purity in the bulk liquid drug substance formulation and greater than 90% radiochemical purity in the reconstituted lyophilized drug product.

Figure 2:
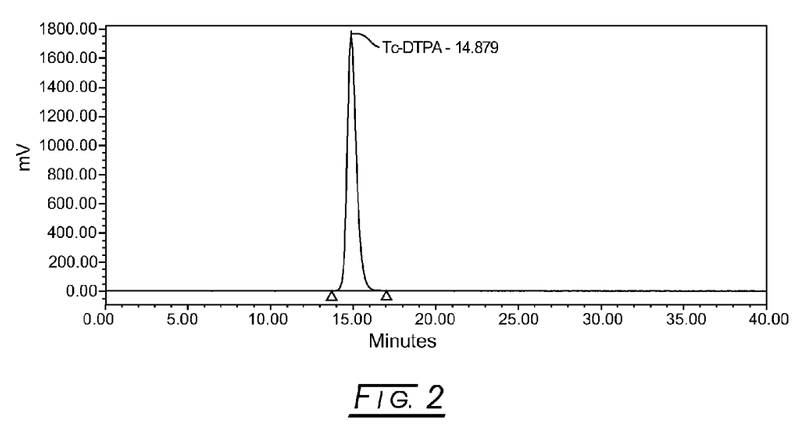
FIG. 2 displays a typical elution profile for $^{99m}$Technetium-labeled DTPA Standard radiolabeled with 10 milliCuries $^{99m}$Tc-pertechnetate using lyophilized Lymphoseek ligand drug product placebo.

FIG. 2 displays a typical elution profile for $^{99m}$Technetium-labeled DTPA Standard radiolabeled with 10 milliCuries $^{99m}$Tc-pertechnetate using lyophilized Lymphoseek Ligand Drug Product Placebo (i.e., 4.5 mM L-Glycine, pH 3, 2.5 mM Sodium L(+)-Ascorbic Acid, 2% (w/v) α,α-Trehalose and 75 μg/mL Stannous Chloride Dihydrate), measured by a Radioactivity (NaI) Detector using SEC radiochemical purity method, described above. The $^{99m}$Tc-DTPA peak retention time is about 15 minutes, eluting between 14 and 16 minutes, which are the approximate retention times for almost all of the $^{99m}$Tc-labeled low-molecular-weight excipients (data not shown).

Example 2

Initial Pilot Formulation

Investigating Interfering Excipients

Figure 3:
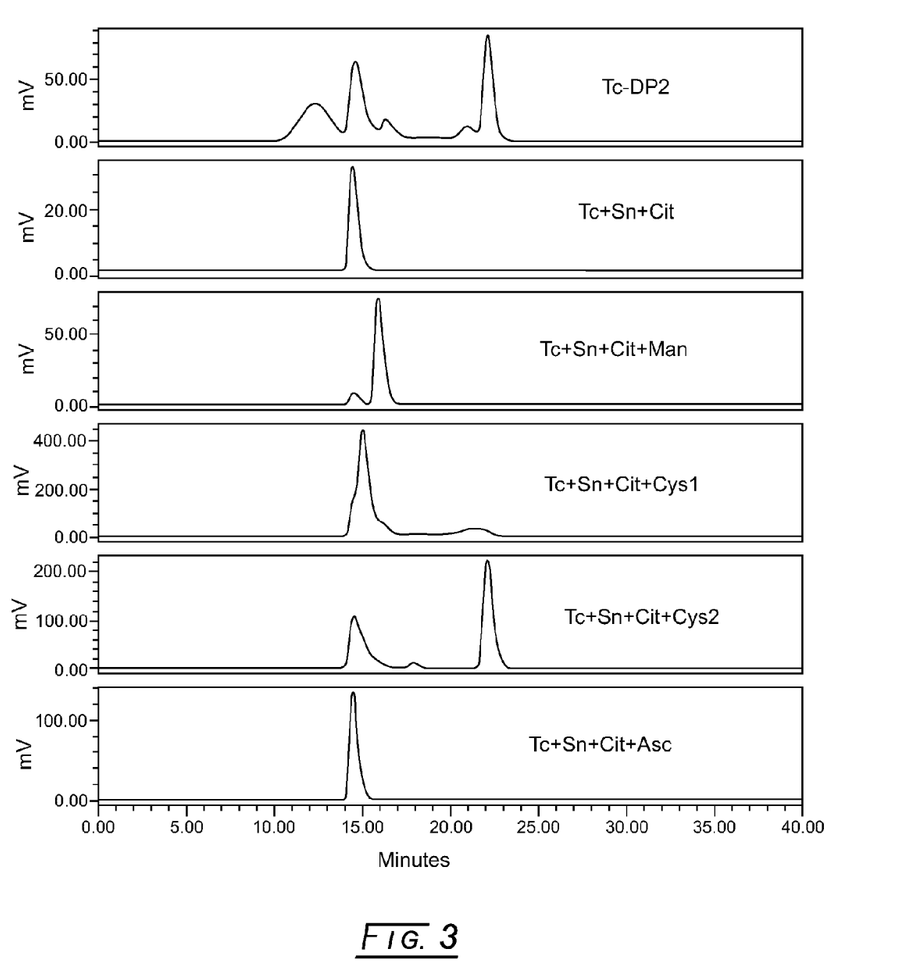
FIG. 3 shows that three excipients (Citrate, Mannitol and L-Cysteine) of the initial pilot formulation display significant $^{99m}$Tc-labeled peaks.

In FIG. 3, the topmost stacked radiochemical elution profile shows the initial lyophilized formulation pilot (5 μM (0.1 mg/mL) DTPA-mannosyl-dextran, 20 mM Sodium Citrate, pH 5.6, 5.7 mM Sodium L-Cysteine, 2% (w/v) D-Mannitol and 75 μg/mL Stannous Chloride, Dihydrate) reconstituted with 10 milliCuries $^{99m}$Tc-pertechnetate and run via the SEC radiochemical purity method. (The initial lyophilized drug product formulation pilot just preceded the development of the SEC radiochemical purity method.) This elution profile clearly shows that the $^{99m}$Tc-DMD peak has less than about 25% radiochemical purity.

The following screening method (in the order of addition) was employed to determine potential interfering excipients in pilot formulations: (1) for drug substance placebo formulations, add 50 μL degassed saline to a 1.5 mL plastic test tube with a cap; for drug substance formulations, add 50 μL of 1.2 mg/mL DTPA-mannosyl-dextran in degassed saline for a final concentration of 0.3 mg/mL DMD; (2) for testing different excipients, add 50 µL of a four-fold concentrated, degassed solution; (3) for reduction of $^{99m}$Tc-pertechnetate, add 50 µL of 300 µg/mL of Stannous Chloride, Dihydrate in 0.01 N degassed Hydrochloric Acid; and immediately following the addition of $SnCL_2$, (4) for radio-labeling the formulation with reduced $^{99m}$Technetium, add 50 µL of 50 milliCuries of $^{99m}$Tc-pertechnetate for a final concentration of 12.5 mCi $^{99m}$Tc-pertechnetate. (Note: Solutions were degassed by bubbling nitrogen gas for at least one hour.) Then, mix and let stand at ambient temperature at least 10 minutes before transferring to a capped HPLC autosampler vial to perform the SEC radiochemical purity assay.

FIG. 3 shows that three excipients of the initial pilot formulation display significant $^{99m}$Tc-labeled peaks. Proceeding from the topmost stacked radiochemical elution profile in a downward manner, the second elution profile shows a substantial $^{99m}$Tc-Citrate peak at RT~14.5 min, which may account for a significant amount of the $^{99m}$Tc-labeled interference at RT~14.5 min in the topmost pattern. Citrate is a known transchelator of DTPA at a pH range of 5 to 6 (Hnatowich, D. J., Chapter 8, pg. 175, *Cancer Imaging with Radiolabeled Antibodies* (Goldenberg, D. M., ed., 1990: Kluwer Academic Publishers, Boston/Dordrecht/London)), but it appears to be too strong to use in the current formulation. In the third radiochemical elution profile, it appears that D-Mannitol competes for $^{99m}$Tc, eluting at RT~16 min. This unexpected interference may be due to the impurities present in this natural product. In the fourth and fifth radiochemical elution profiles, two different L-Cysteine concentrations were employed: 0.25 and 1.0 mg/mL L-Cysteine in the final concentration, respectively. While the fourth elution profile displays some interference binding, the fifth elution profile at 1 mg/mL L-Cysteine clearly shows that Cysteine binds $^{99m}$Tc and interferes with the transchelation of Citrate, eluting at retention times ranging from 21 to 23 minutes. The sixth radiochemical elution profile involves the addition of 1 mg/mL sodium L(+)-Ascorbic Acid Dihydrate to a Citrate formulation; Ascorbic Acid does not appear to interfere with $^{99m}$Tc-Citrate.

Figure 4:
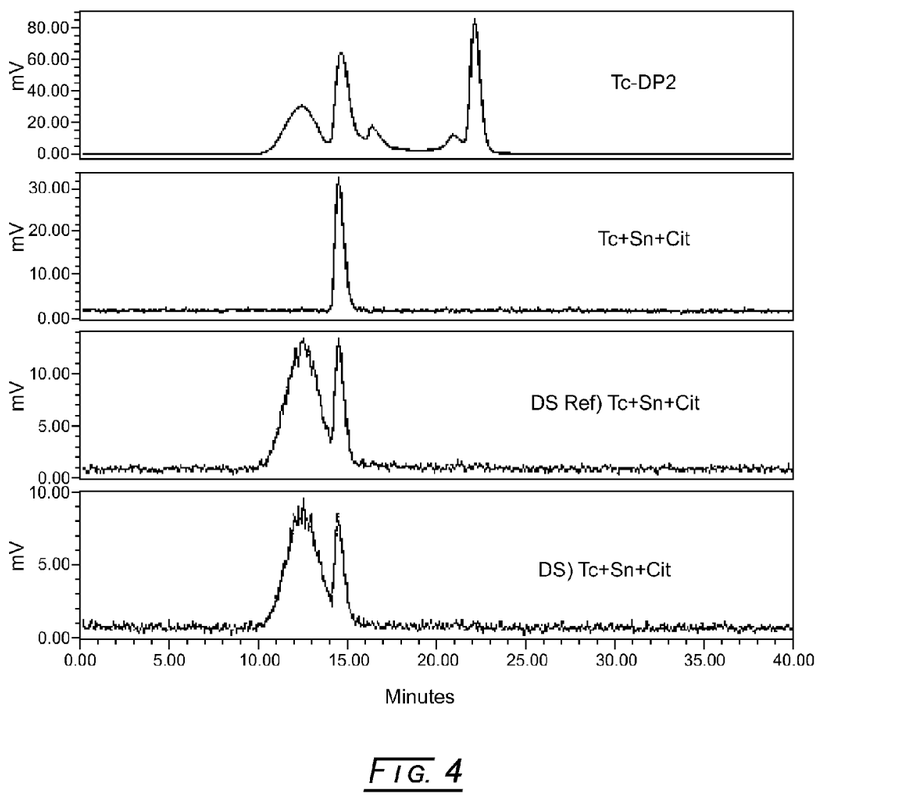
FIG. 4 displays a comparison of the initial drug product formulation with liquid drug substance formulation pilots.

FIG. 4 displays a comparison of the initial drug product formulation with liquid drug substance formulation pilots. The topmost stacked radiochemical elution profile is the initial drug product formulation and the second profile is that of Sodium Citrate in saline with $SnCL_2$ added to reduce 12.5 mCi $^{99m}$Tc-pertechnetate. In the third and fourth radiochemical elution profiles, the DTPA-mannosyl-dextran drug substance is partially radiolabeled with a significant $^{99m}$Tc-Citrate eluting at about 14.5 minutes. Hence, the use of Sodium Citrate is not a suitable pH buffer\transchelator choice.

Example 3

Figure 5:
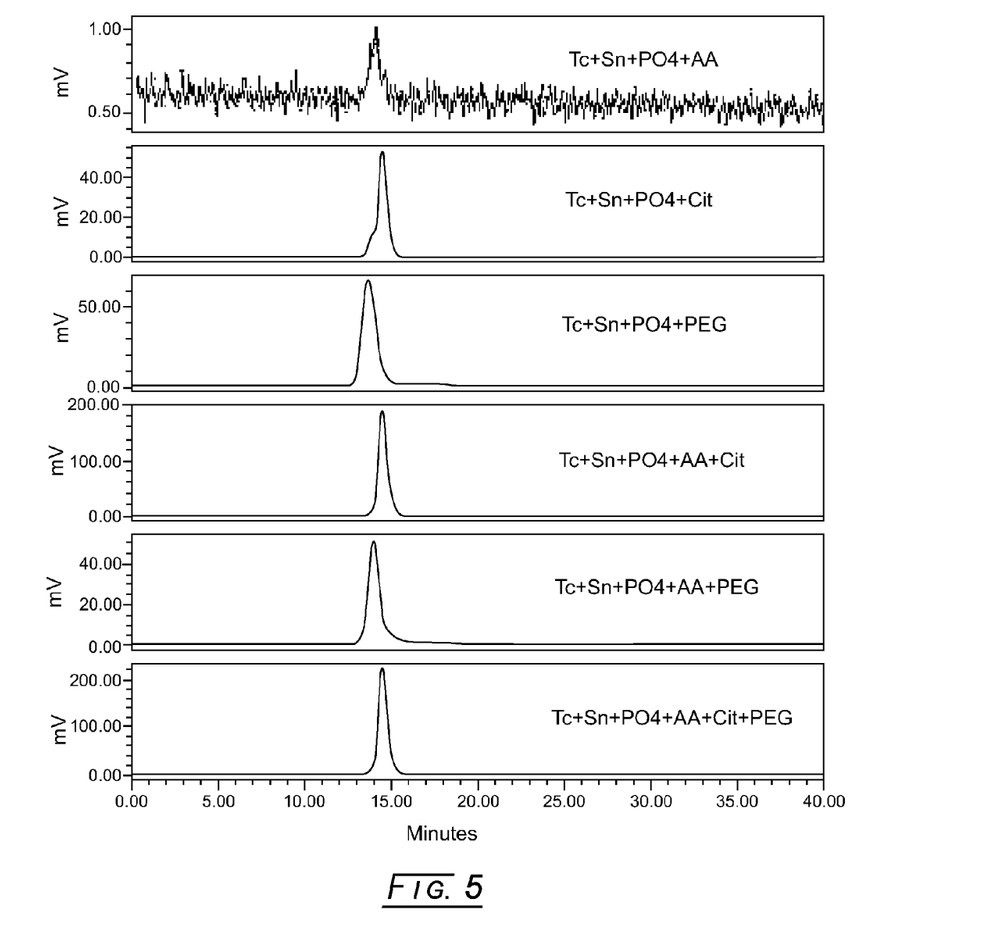
FIG. 5 is a stacked SEC radiochemical elution profile for liquid DTPA-mannosyl-dextran drug substance placebo formulation pilots containing a sodium phosphate pH buffer and different combinations of transchelator (Citrate), reducing agents (Ascorbic Acid) and bulking agents (Polyethylene Glycol (PEG) 8000), as measured by the SEC radiochemical purity method.

Screening for pH Buffers, Transchelator and Bulking Excipients for Enhanced Radiolabeling of DTPA-Mannosyl-Dextran FIG. 5 is a stacked radiochemical elution profile for liquid DTPA-mannosyl-dextran drug substance placebo formulation pilots containing a Sodium Phosphate pH buffer and different combinations of transchelator, reducing agents and bulking agents, as measured by the SEC radiochemical purity method. The topmost stacked radiochemical elution profile shows a small $^{99m}$Tc-labeled interference peak with the 20 mM Sodium Phosphate buffer at pH 4 and 1.5 mg/mL Sodium Ascorbate. The second through the sixth elution profiles shows 20 mM Sodium Phosphate, pH 4, 75 µg/mL $SnCL_2.2H_2O$ and 12.5 mCi $^{99m}$Tc-pertechnetate with the following respective potential excipients: 1 mg/mL Sodium Citrate; 1% PEG 8000; 1 mg/mL Sodium Citrate and 1.5 mg/mL Sodium Ascorbate; 1.5 mg/mL Sodium Ascorbate and 1% PEG 8000; and 1.5 mg/mL Sodium Ascorbate, 1 mg/mL Sodium Citrate and 1% PEG 8000. They all display significant $^{99m}$Tc-labeled interference peaks eluting as early as RT~14 minutes for $^{99m}$Tc-PEG 8000 to a more low-molecular-weight retention time of ~15 minutes for $^{99m}$Tc-Citrate.

Figure 6:
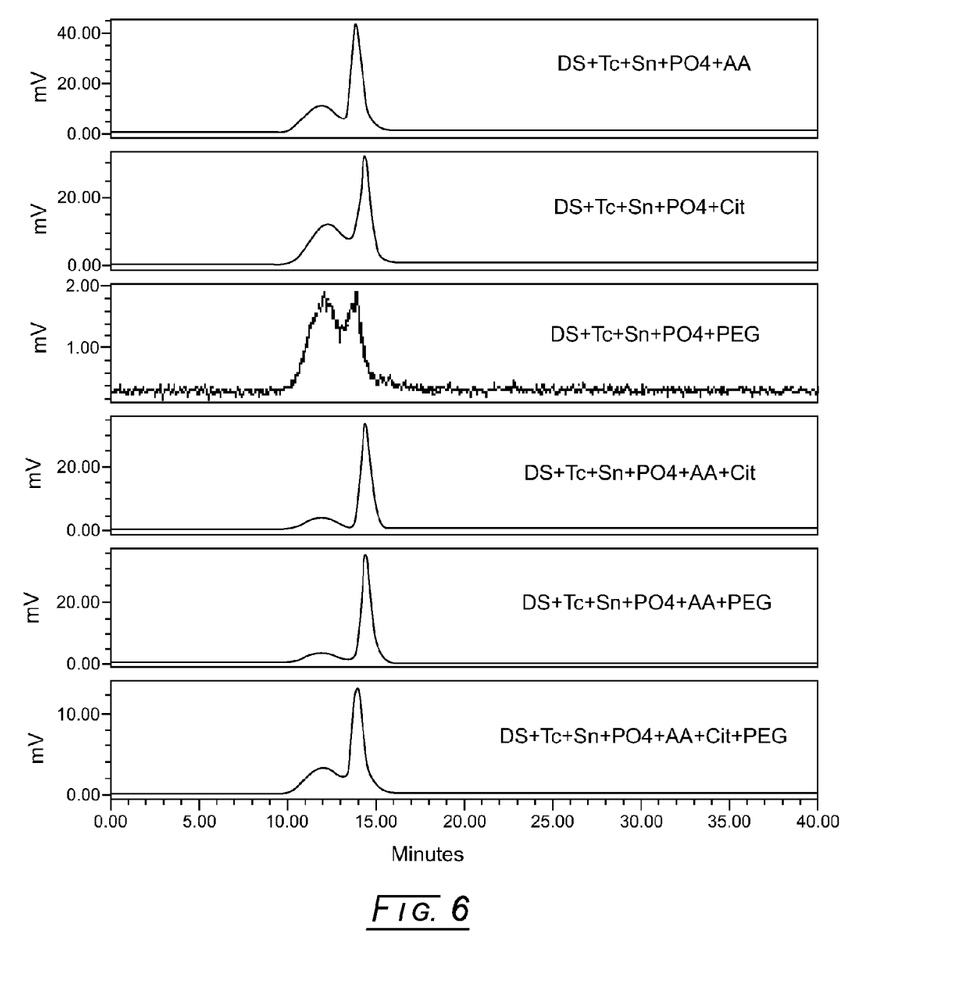
FIG. 6 is a stacked SEC radiochemical elution profiles for the corresponding liquid DTPA-mannosyl-dextran drug substance placebo formulation pilots containing a sodium phosphate pH buffer.

In FIG. 6, the stacked radiochemical elution profiles for the corresponding liquid DTPA-mannosyl-dextran drug substance placebo formulation pilots containing a Sodium Phosphate pH buffer are seen. For DTPA-mannosyl-dextran formulations containing 0.3 mg/mL, or 15 µM DMD in FIG. 6, the stacked radiochemical elution profiles show a little significant radiolabeling of the drug substance. The third profile from the top displays background levels of $^{99m}$Tc-DMD, indicating that phosphate and PEG 8000 do not serve as satisfactory transchelators. At one-fifth its pH buffer strength, Citrate is less efficient in radiolabeling drug substance and still interferes in these formulations. In addition, PEG 8000 apparently interferes with the drug substance yield with its hydroxyl groups and is unsuitable as a bulking agent. Since Sodium Phosphate is not an ideal pH buffer for lyophilization, alternative generally recognized as safe (GRAS) pH buffers were screened.

Figure 7A:
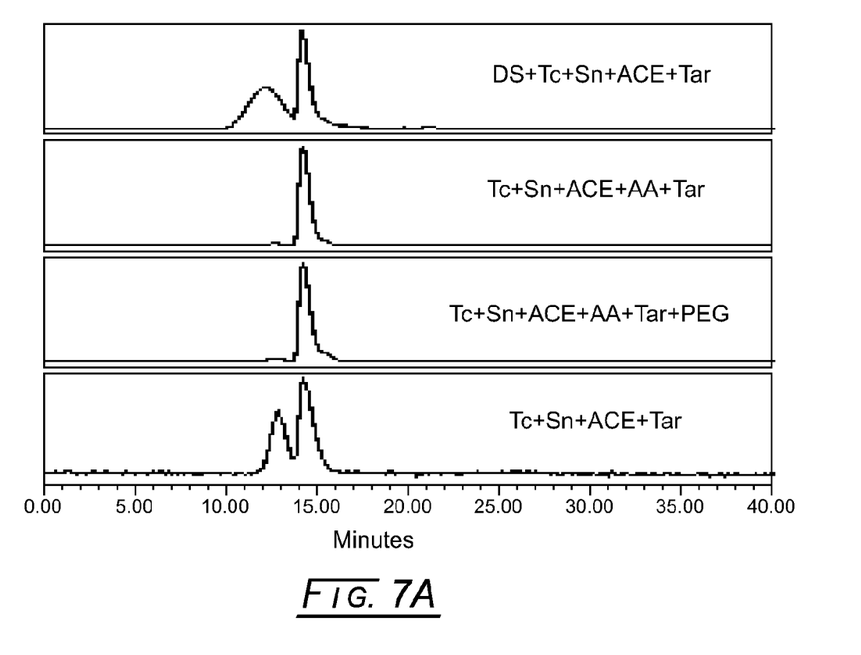
FIGS. 7A and 7B are the stacked SEC radiochemical elution profiles for liquid DTPA-mannosyl-dextran drug substance and placebo formulation pilots containing 20 mM sodium acetate buffer (ACE) at pH 4, Tartrate and PEG 8000.
Figure 7B:
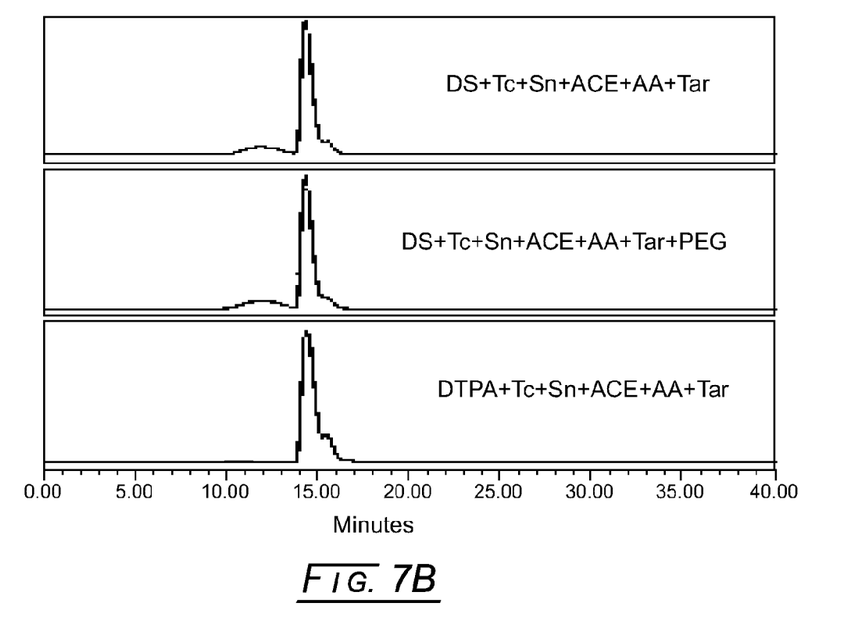

In FIGS. 7A and 7B, the stacked radiochemical elution profile for liquid DTPA-mannosyl-dextran drug substance and placebo formulation pilots containing 20 mM Sodium Acetate buffer at pH 4 are interspersed. In FIG. 7A, the topmost radiochemical elution profile is the drug substance formulation with the potential transchelator, Sodium Tartrate at 1.5 mg/mL, displaying an enhanced radiolabeling of the drug substance with a significant interfering peak, $^{99m}$Tc-Tartrate (see fourth elution profile for corresponding placebo formulation). The second and third elution profiles in FIG. 7A show little difference in the presence of Sodium Ascorbate and PEG 8000. In FIG. 7B, the radiochemical elution profiles demonstrate that the drug substance formulations for the Sodium Ascorbate and PEG 8000 combinations with Tartrate have less efficiency in radiolabeling the drug substance. Finally, the DTPA Standard has a small tailing edge shoulder with Sodium Acetate and Sodium Ascorbate at pH 4. Hence, the selection of Sodium Tartrate as potential transchelator in an Acetate pH buffer is unsatisfactory.

Figure 8:
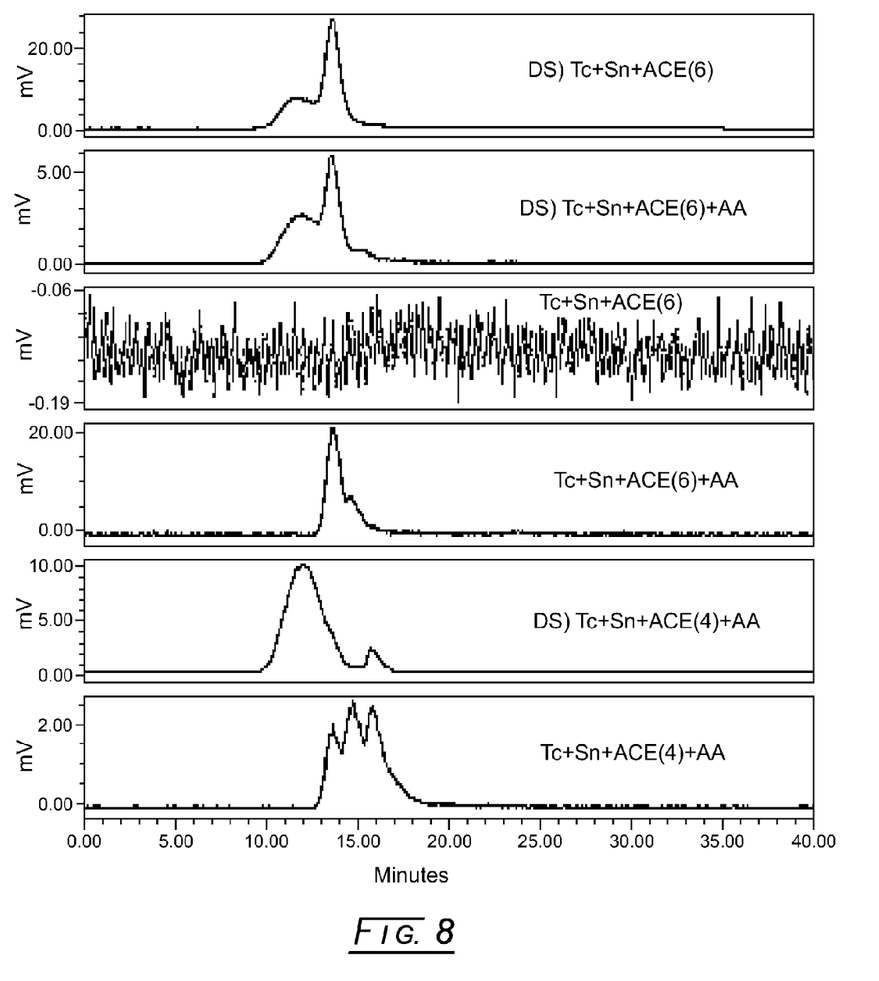
FIG. 8 are stacked SEC radiochemical elution profiles for liquid DTPA-mannosyl-dextran drug substance and placebo formulation pilots containing 20 mM sodium acetate buffer at pH 4 and 6.

In FIG. 8, the stacked radiochemical elution profile for liquid DTPA-mannosyl-dextran drug substance and placebo formulation pilots containing 20 mM Sodium Acetate buffer at pH 4 and 6 are also interspersed. The topmost and second radiochemical elution profiles show at pH 6, the presence of 1.5 mg/mL Sodium Ascorbate enhances the radiochemical purity of the drug substance, but the third and fourth profiles indicate that Ascorbate may contribute to a significant and a smaller interference peak of $^{99m}$Tc-Ascorbate at RT~13.5 and ~15 minutes, respectively. The fifth elution profile demonstrates that the radiochemical purity is pH-sensitive, primarily radiolabeling the drug substance at pH 4 in the presence of Sodium Ascorbate. The fifth profile may contain some interfering material co-eluting with the $^{99m}$Tc-DMD peak, as observed in the slight shoulder of the trailing edge of the drug substance peak as well as the small $^{99m}$Tc-labeled peak at RT~16 minutes.

Figure 9A:
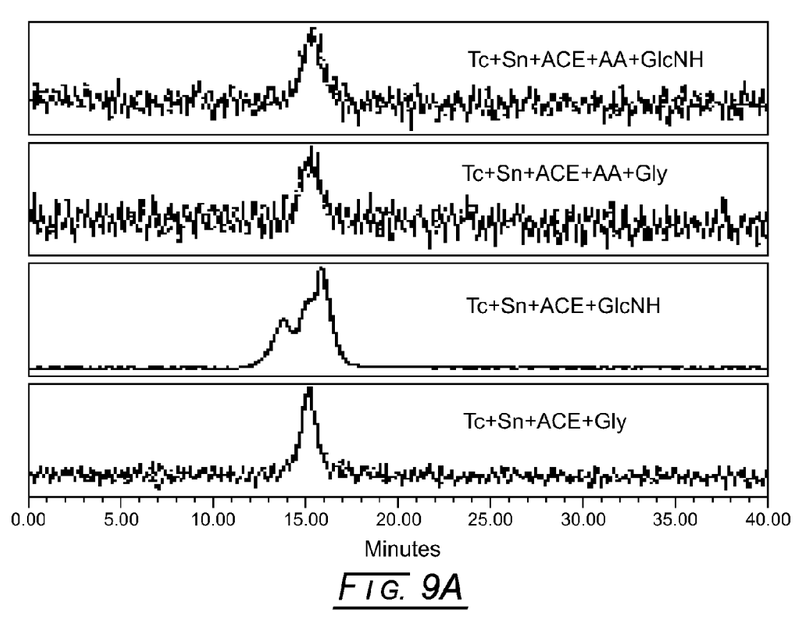
FIGS. 9A and 9B are screening studies employing a reducing sugar with a primary amine and a zwitterionic amino acid, i.e., Sodium Glucosamine (GlcNH) and Glycine (Gly)
Figure 9B:
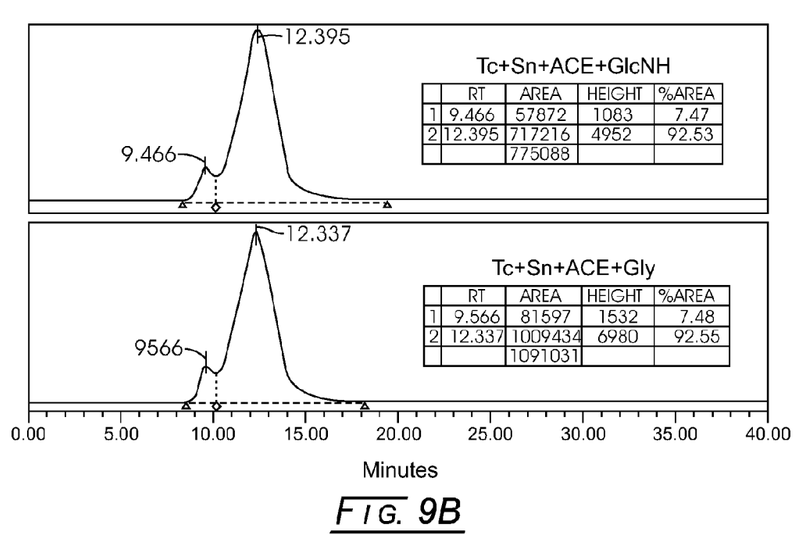

In FIGS. 9A and 9B, screening studies employing a reducing sugar with a primary amine and a zwitterionic amino acid, i.e., Sodium Glucosamine and Glycine, were conducted on an educated guess that these excipients would have some transient interactions with $^{99m}$Technetium, because this radioisotope forms stable complexes with amine and amide nitrogens, carboxylate oxygens, and thiolate and thioether sulfurs with a strong preference for thiolate sulfurs (Giblin, M. F. et al. (1998) *PNAS USA* 95, 12814-12818). FIG. 9A displays the liquid DTPA-mannosyl-dextran drug substance placebo formulation pilots with 20 mM Sodium Acetate buffer at pH 4 with either 1.5 mg/mL Sodium Glucosamine and Glycine in the absence and presence of Sodium Ascorbate (1.5 mg/mL). These excipients display background level radioactivity with small $^{99m}$Tc-labeled peaks at RT~15 minutes, except for the third elution profile for just Sodium Glucosamine, which has greater than background radioactivity. In FIG. 9B, the stacked radiochemical elution profiles for the liquid drug substance formulation pilots with 20 mM Sodium Acetate buffer, pH 4, and either 1.5 mg/mL Sodium Glucosamine, or Glycine are nearly identical, demonstrating an ability to efficiently radiolabel the $^{99m}$Tc-DMD peak (at RT 12.4 min) as transchelators. Because Sodium Glucosamine is not a GRAS excipient, it was not pursued in subsequent formulations. Glycine was identified as a potential, non-interfering transchelator.

Figure 10A:
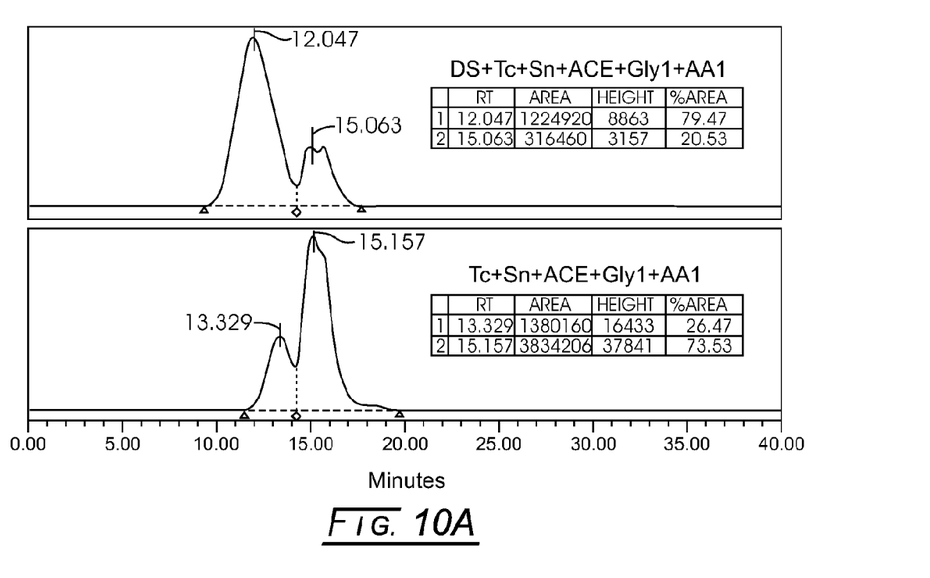
FIGS. 10A and 10B are studies relating to the range of the excipients Glycine and Sodium Ascorbate at two final concentrations: for $Gly_1$ and $Gly_2$, it is 0.5 and 2.0 mg Glycine/mL, respectively; and for $AA_1$ and $AA_2$, it is 1.5 and 0.38 mg/mL Sodium Ascorbate, respectively.
Figure 10B:
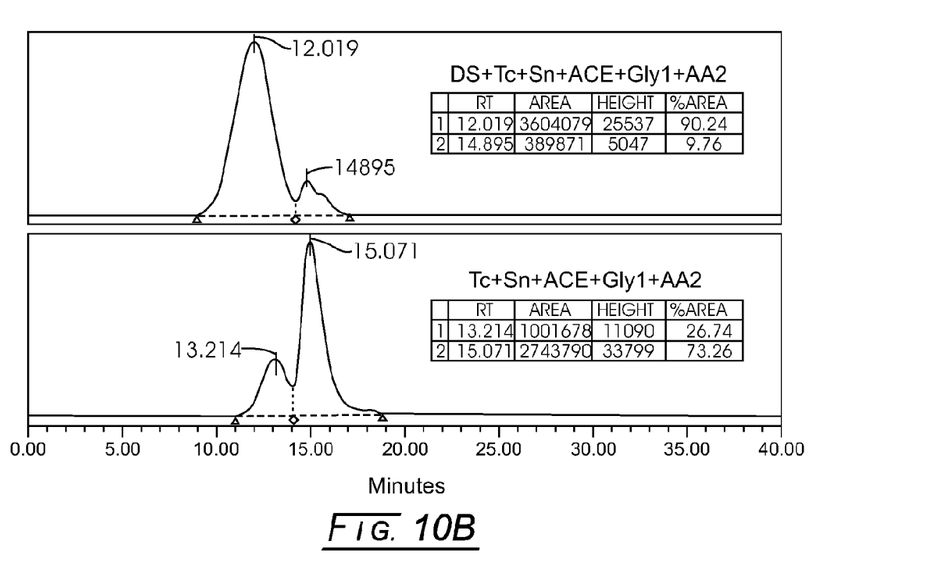

Since Glycine and Sodium Ascorbate appeared compatible with enhanced radiochemical purity of the drug substance, the range of these excipients was investigated. Glycine and Sodium Ascorbate were evaluated at two final concentrations: for $Gly_1$ and $Gly_2$, it is 0.5 and 2.0 mg/mL, respectively; and for $AA_1$ and $AA_2$, it is 1.5 and 0.38 mg/mL, respectively. For the Glycine #1 and 2 drug substance formulations (i.e., 15 µM DTPA-mannosyl-dextran, 20 mM Sodium Acetate, pH 4, 75 µg/mL $SnCL_2.2H_2O$ and 12.5 mCi $^{99m}$Tc-pertechnetate), the mean average of two radiolabeling studies for $Gly_1$ and $Gly_2$ are 90.7 and 88.7% $^{99m}$Tc-DMD, respectively, as measured by the SEC radiochemical purity method. In the presence of $Gly_1$, the mean average of two radiolabeling studies for the $AA_1$ and $AA_2$ drug substance formulations are 80.3 and 90.3% $^{99m}$Tc-DMD purity, respectively (see FIGS. 10A and 10B).

Figure 11:
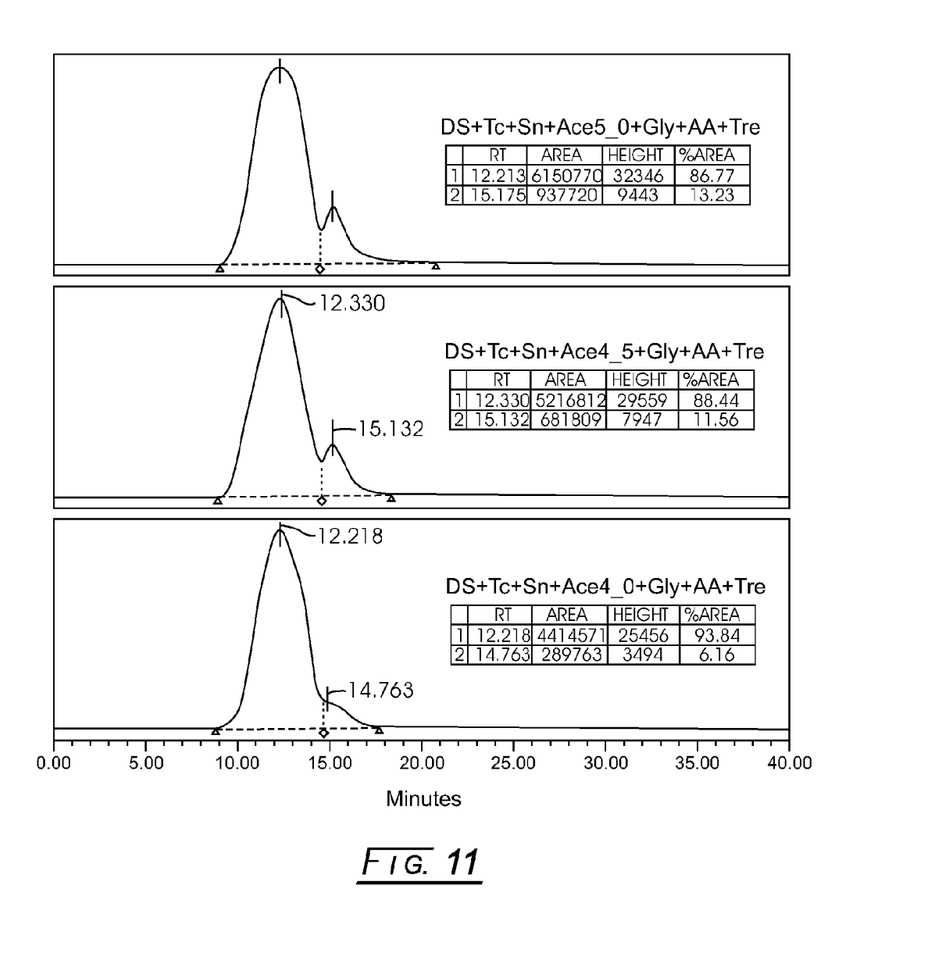
FIG. 11 are stacked SEC radiochemical elution profiles for the liquid drug substance formulation pilots with 20 mM sodium acetate buffer ranging from pH 5 to 4 with Glycine, Sodium Ascorbate and α,α-Trehalose.

The screening for suitable bulking agents for lyophilization was conducted in 20 mM Sodium Acetate, pH 4 to 5, formulations containing Glycine as a transchelator and Sodium Ascorbate as an antioxidant\reducing agent. It was determined that polymeric excipients, such as, PEG 2000 and Polyvinylpyrrolidone interfered with the efficiency of radiolabeling DTPA-mannosyl-dextran (data not shown). Finally, α,α-Trehalose (2% w/v) was identified as a potential non-interfering bulking agent for the liquid drug substance formulation. In FIG. 11, the stacked radiochemical elution profiles for the liquid drug substance formulation pilots with 20 mM Sodium Acetate buffer ranging from pH 5 to 4 with Glycine and Sodium Ascorbate shows that 2% α,α-Trehalose has little, if any, interference in the radiochemical purity of $^{99m}$Tc-DMD. Furthermore, there is significant pH sensitivity in the Sodium Acetate formulations (15 µM DTPA-mannosyl-dextran, 20 mM Sodium Acetate, 1 mg/mL Glycine, 1 mg/mL Sodium Ascorbate, 2% (w/v) α,α-Trehalose, 38.5 mM Sodium Chloride, 75 µg/mL $SnCL_2.2H_2O$ and 12.5 mCi $^{99m}$Tc-pertechnetate), giving 86.8, 88.4 and 93.8% $^{99m}$Tc-DMD purity for pH 5.0, 4.5 and 4.0, respectively. Hence, the screening process for identifying suitable excipients for potential use in a lyophilized drug product kit formulation was completed. The next step is to optimize the formulation, demonstrate the feasibility of the lyophilized kit format and develop a reconstitution procedure.

Example 4

Figure 12:
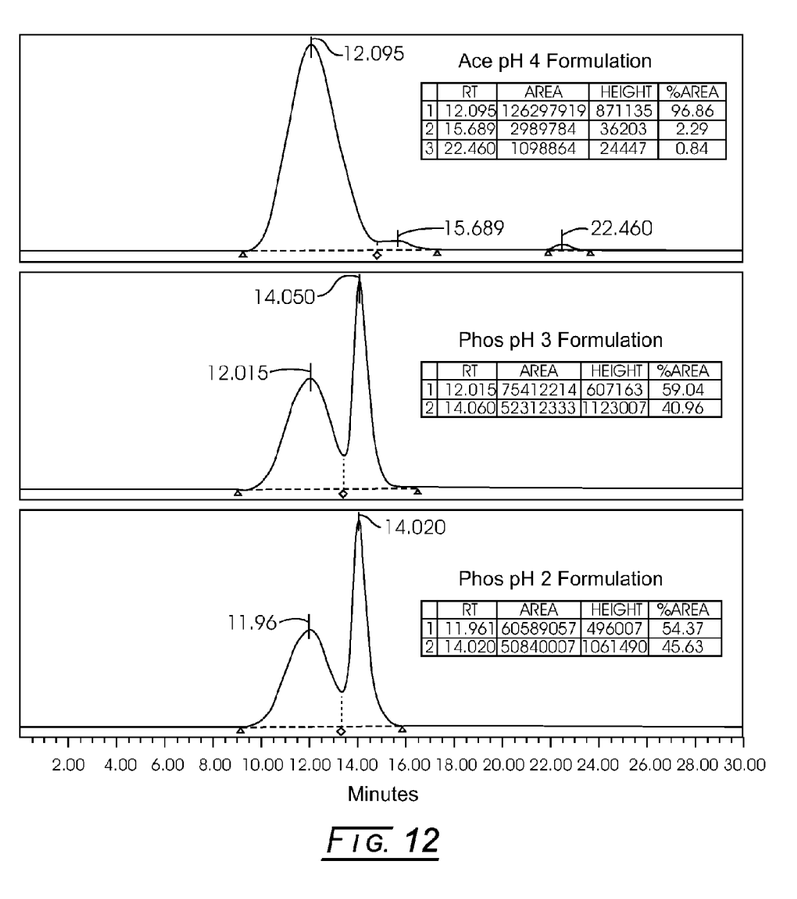
FIG. 12 are stacked SEC radiochemical elution profiles for the DMD drug substance formulations (containing 25 μM DTPA-mannosyl-dextran (0.5 mg/mL), pH buffer, 0.5 mg/mL Glycine, 0.5 mg/mL Sodium Ascorbate, 2% (w/v) α,α-Trehalose, 38.5 mm Sodium Chloride and 75 μg/mL $SnCL_2.2H_2O$) with the addition of 12.5 mCi $^{99m}$Tc-pertechnetate. The pH buffer is Acetate, pH 4; Phosphate, pH 3; and Phosphate, pH 2 (from top panel to bottom)
Figure 13:
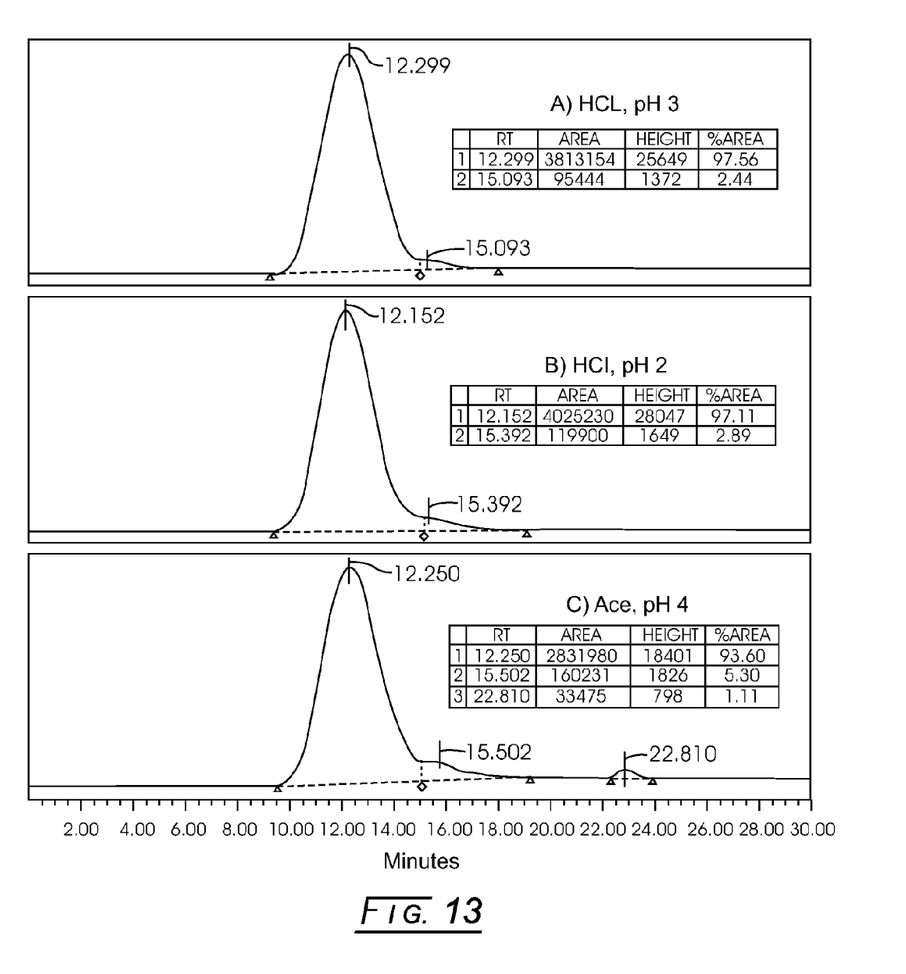
FIG. 13 displays the stacked SEC radiochemical elution profiles for the DMD drug substance formulations at pH 3, 2 and 4 containing the following excipients: 25 μM DTPA-mannosyl-dextran (0.5 mg/mL), 0.5 mg/mL Glycine, 0.5 mg/mL Sodium Ascorbate, 2% (w/v) α,α-Trehalose and 75 μg/mL $SnCL_2.2H_2O$ (with 10 mM Sodium Acetate at pH 4).

Optimizing the Formulation for Enhanced Radiolabeling of Lyophilized DTPA-Mannosyl-Dextran Drug Product The apparent pH sensitivity of the Acetate buffer formulations, giving improved radiochemical purity for $^{99m}$Tc-DMD at decreasing pH, needed to be explored. The initial pH studies employed 10 mM Sodium Phosphate at pH 2 and 3 and as a control, 20 mM Sodium Acetate at pH 4. FIG. 12 shows the stacked radiochemical elution profiles for the DMD drug substance formulations (containing 25 µM DTPA-mannosyl-dextran (0.5 mg/mL), pH buffer, 0.5 mg/mL Glycine, 0.5 mg/mL Sodium Ascorbate, 2% (w/v) α,α-Trehalose, 38.5 mM Sodium Chloride and 75 µg/mL $SnCL_2.2H_2O$) with the addition of 12.5 mCi $^{99m}$Tc-pertechnetate. The topmost elution profile displays the Acetate formulation at pH 4, which has 96.9% $^{99m}$Tc-DMD purity, as measured by the SEC radiochemical purity method. This formulation meets our goal for liquid drug substance formulation (i.e., greater than 95% $^{99m}$Tc-DMD purity). Unfortunately, the 10 mM Sodium Phosphate formulations at pH 3 and 2 have substantial $^{99m}$Tc-labeled interference peaks at RT~14.0 minutes (see FIG. 12). Thus, it was determined that Glycine/Hydrochloric Acid should serve as a suitable acidic pH buffer as well as a potential non-interfering transchelator. FIG. 13 displays the stacked radiochemical elution profiles for the DMD drug substance formulations at pH 3, 2 and 4 containing the following excipients: 25 µM DTPA-mannosyl-dextran (0.5 mg/mL), 0.5 mg/mL Glycine, 0.5 mg/mL Sodium Ascorbate, 2% (w/v) α,α-Trehalose and 75 µg/mL $SnCL_2.2H_2O$ (with 10 mM Sodium Acetate at pH 4). It was fortuitous to employ Glycine Hydrochloride as an acidic pH buffer and a transchelator, because the pH 3 and pH 2 drug substance formulations exhibit 97.6 and 97.1% $^{99m}$Tc-DMD purity, respectively, and meeting the desired goal of the drug substance formulation (see FIG. 13). In FIG. 13, the Acetate formulation at pH 4 failed to meet the goal for drug substance formulation (93.6% versus >95% $^{99m}$Tc-DMD purity), but this may due to day-to-day variability in the preparation of the formulation, incomplete degassing of the solutions, the inadequate mixing of the Stannous Chloride Dihydrate, etc. The Glycine Hydrochloride buffer may be utilized in pH 4 formulations in addition to the Acetate buffer.

The Class I glass vials were filled with sterile-filtered aliquots of this pH study, 1.05 mL, into 3 mL vials. Stoppers were placed in the necks of these vials, and the vials were placed on the VirTis Lyophilizer shelves for lyophilization. After the lyophilization cycle was completed, the vials were backfilled with nitrogen gas and stoppered. Subsequently, the stoppered vials were crimped with aluminum seals. On visual inspection, the lyophilized cakes for the Acetate, pH 4, and the Glycine, pH 3, drug product formulation vials retained their amorphous structure and appeared to have dried to low residual moisture. In contrast, the Glycine, pH 2, drug product formulation vials were totally collapsed (i.e., devoid of structure). The preferred embodiment of this invention is the pH 3 drug product formulation (i.e., 12.5 to 25 µM DTPA-mannosyl-dextran (0.25 to 0.5 mg/mL), 0.5 mg/mL Glycine, pH 3, 0.5 mg/mL Sodium Ascorbate, 2% (w/v) α,α-Trehalose and 75 µg/mL $SnCL_2.2H_2O$).

Example 5

Developing the Reconstitution Procedure, Including Using a Phosphate-Buffered Saline Diluent, for Improved Ease-of-Use in Radiolabeling Lyophilized DTPA-Mannosyl-Dextran Drug Product Due the final pH of the Lymphoseek Ligand Drug Product formulation, about pH 3, which is lower than the recommended pH for parenteral drugs (Stranz, M. and Kastango, E. S. (2002) *Int. J. Pharm. Compound.* 6(3), 216-220), it was decided to utilize a Diluent that neutralizes pH following the reconstitution with $^{99m}$Tc-pertechnetate to a less painful and harmless pH (e.g., between pH 5 and 9). Sodium $^{99m}$Tc-pertechnetate is eluted from a Molybdenum-99 generator with 0.9% Sodium Chloride, or isotonic saline. The Lymphoseek Ligand Drug Product is formulated to meet the recommendations of the Infusion Nursing Society to be less than 500 mOsm\L following reconstitution with 1 mL of Sodium $^{99m}$Tc-pertechnetate. A suitable Diluent was identified for use with human parenterals, Buffered Saline for Injection from Greer Laboratories. The formulation of this Diluent is: 0.107% Sodium Phosphate, Heptahydrate, 0.036% Potassium Phosphate (desirably USP—NF, United States Pharmacopeia—National Formulary), 0.5% Sodium Chloride and 0.4% Phenol. It is recommended that the lyophilized Lymphoseek Ligand Drug Product vial is reconstituted with 0.7 cc of 10 to 50 mCi of Sodium $^{99m}$Tc-pertechnetate for at least 10 minutes at ambient room temperature, mixed intermittently and then, diluted with 0.3 cc of Buffered Saline for Injection. The Lymphoseek® Ligand Drug Product has at least twelve hours of reconstituted stability, but it is recommended that the reconstituted drug product be administered within six hours (data not shown). Hence, the neutralized $^{99m}$Tc-labeled Lymphoseek Ligand Drug Product should be well tolerated by patients upon intradermal injection.

While the process, composition, and kit have been described with reference to various embodiments, those skilled in the art will understand that various changes may be made and equivalents may be substituted for elements thereof without departing from the scope and essence of the disclosure. Additionally, many modifications may be made to adapt a particular situation or material to the teachings of the disclosure without departing from the essential scope thereof. Therefore, it is intended that the disclosure may not be limited to the particular embodiments disclosed, but that the disclosure will include all embodiments falling within the scope of the appended claims. In this application the US measurement system is used, unless otherwise expressly indicated. Also, all citations referred to herein are expressly incorporated herein by reference.

What is claimed is:

1. A method for stabilizing a DTPA-dextran cold kit for long-term storage, compromising the steps of:
    (a) adding an aqueous composition, compromising:
        (i) a sugar selected from the group of non-reducing disaccharides with a concentration up to 2% (w/v);
        (ii) a pH buffer selected from a group of pH buffers in concentration range of up to about 0.5 mg/mL;
    to a vessel containing about 90% of its target volume of degassed and deaerated water for injection;
    (b) adding a non-sulfhydryl anti-oxidant wherein the concentration is in the range of about 0.5 mg/mL;
    (c) adjusting the solution pH to a target pH of 3.2±0.2 with 6 N hydrochloric acid, while maintaining an inert gas sparge;
    (d) adding a stannous salt wherein the concentration of the dihydrate form of the stannous salt is up to 75 micrograms/mL;
    (e) adding a DTPA-dextran with a concentration of up to 0.50 mg/mL;
    (f) adjusting the solution pH to a target pH of 3.2±0.2 with 6 N hydrochloric acid, while maintaining an inert gas sparge;
    (g) adjusting the volume of the formulation to 100% of its target volume with degassed and deaerated water for injection;
    (h) filtering the aqueous composition through a 0.22 micron filter and filling the aqueous composition in to glass vials with 1.0 mL±10%;
    (i) removing the majority of the water content of the product, decreasing the residual moisture to about less than 1% water content by lyophilization;
    (j) backfilling the lyophilized product with an inert gas to about 11.5 p.s.i. prior to stoppering the vials;
    (k) crimping the lyophilized product vials with aluminum seals; and
    (l) storing the crimped-sealed lyophilized product vials at either 2° to 8° C. or 25°.

2. The method of claim 1, wherein the non-reducing disaccharide is α,α-Trehalose Dihydrate.

3. The method of claim 1, wherein the pH buffer is Glycine.

4. The method of claim 1, wherein the non-sulfhydryl anti-oxidant is L(+)-Ascorbic Acid Sodium salt.

5. The method of claim 1, wherein the stannous salt is Stannous Chloride Dihydrate.

6. The method of claim 1, wherein the DTPA-dextran contains multiple DTPA groups conjugated to dextran in the molar ratio range of about 2:1 to 12:1.

7. The method of claim 1, wherein the DTPA-dextran contains dextran in the average molecular weight range of about 5,000 to 20,000 Daltons.

8. The method of claim 1, wherein the DTPA-mannosyl-dextran containing a molar ratio range of about 2:1 to 12:1 conjugated mannose groups to DTPA-dextran.

* * * * *